(12) United States Patent
Srinivasan (10) Patent No.: US 10,966,861 B2
(45) Date of Patent: Apr. 6, 2021

(54) APPARATUS AND METHOD FOR MAINTAINING ENTHALPY WITH SECONDARY MECHANISMS

(71) Applicant: Swathi R. Srinivasan, Beachwood, OH (US)

(72) Inventor: Swathi R. Srinivasan, Beachwood, OH (US)

(*) Notice: Subject to any disclaimer, the term of this patent is extended or adjusted under 35 U.S.C. 154(b) by 451 days.

(21) Appl. No.: 15/419,025

(22) Filed: Jan. 30, 2017

(65) Prior Publication Data

US 2017/0216087 A1 Aug. 3, 2017

Related U.S. Application Data

(60) Provisional application No. 62/288,480, filed on Jan. 29, 2016.

(51) Int. Cl.
A61F 7/00 (2006.01)
A61F 7/02 (2006.01)
A61G 11/00 (2006.01)

(52) U.S. Cl.
CPC .............. *A61F 7/007* (2013.01); *A61F 7/02* (2013.01); *A61G 11/00* (2013.01); *A61F 2007/008* (2013.01); *A61F 2007/0071* (2013.01); *A61F 2007/0075* (2013.01); *A61F 2007/0078* (2013.01); *A61F 2007/0079* (2013.01); *A61F 2007/0086* (2013.01); *A61F 2007/0096* (2013.01); *A61F 2007/0292* (2013.01); *A61G 2210/90* (2013.01)

(58) Field of Classification Search
CPC .............. A61F 7/007; A61F 2007/0071; A61F 2007/0077; A61F 2007/0078; A61F 2007/0079; A61F 2007/008; A61F 2007/0086; A61F 2007/0095; A61F 2007/0096; A61F 2007/0097; A61F 7/02; A61F 2007/0244; A61F 2007/0292; A61G 11/00; A61G 2210/90

See application file for complete search history.

(56) References Cited

U.S. PATENT DOCUMENTS

| 5,058,563 | A | 10/1991 | Manker |
| 5,932,129 | A * | 8/1999 | Hyatt ..................... A61F 7/007 |
| | | | 126/263.01 |
| 7,934,537 | B2 | 5/2011 | Kolowich |
| 8,257,417 | B2 | 9/2012 | Chen et al. |

(Continued)

OTHER PUBLICATIONS

Preterm Birth, Fact Sheet, available at http://www.who.int/mediacentre/factsheets/fs363/en/, (Nov. 2016).

(Continued)

*Primary Examiner* — Linda C Dvorak
*Assistant Examiner* — Bradford C. Blaise
(74) *Attorney, Agent, or Firm* — Kusner & Jaffe (57) ABSTRACT

An interactive enthalpy exchange system for infant care includes a pouch for receiving an infant, and a heat source arranged in the pouch. The heat source includes a first heat source and a second heat source different from the first heat source. Control circuitry is operatively coupled to the heat source, the control circuitry configured to control interactive enthalpy between the first heat source and the second heat source to maintain a temperature within the pouch at a prescribed temperature.

22 Claims, 9 Drawing Sheets

(56) References Cited

U.S. PATENT DOCUMENTS

| | | | |
|---|---|---|---|
| 8,834,548 B2 | 9/2014 | Liang et al. | |
| 2005/0021115 A1* | 1/2005 | Yue | A61F 7/007 607/114 |
| 2005/0280682 A1* | 12/2005 | Kato | B41J 11/002 347/102 |
| 2010/0168502 A1* | 7/2010 | Delaporte | A61G 11/00 600/22 |
| 2011/0021886 A1* | 1/2011 | Briggs | A61B 5/01 600/301 |
| 2011/0046433 A1* | 2/2011 | Khodak | A61F 7/007 600/22 |
| 2011/0238143 A1* | 9/2011 | Schock | A61F 7/0053 607/104 |
| 2012/0078034 A1* | 3/2012 | Falk | A61G 11/00 600/22 |
| 2014/0303694 A1* | 10/2014 | Timme | A61M 16/024 607/96 |
| 2015/0066119 A1 | 3/2015 | Panicker et al. | |
| 2015/0107601 A1* | 4/2015 | Arnone | A61F 7/03 128/845 |
| 2016/0008165 A1* | 1/2016 | Baelden | A61F 7/007 219/212 |
| 2016/0051403 A1* | 2/2016 | Thomas | A61G 11/00 607/112 |
| 2016/0278976 A1* | 9/2016 | Kruger | A44B 18/0076 |
| 2017/0087799 A1* | 3/2017 | Buttner | B32B 5/02 |

OTHER PUBLICATIONS

Blencowe, H. et al., National, Regional and Worldwide Estimates of Preterm Birth, The Lancet, Jun. 2012.
World Health Organization (WHO), WHO Recommendations on Interventions to Improve Preterm Birth Outcomes, 2015.
Wariki WMV and Mori R., Interventions to Prevent Hypothermia at Birth in Preterm and/or Low-birth-weight Infants: RHL commentary, Jun. 1, 2010, The WHO Reproductive Health Library, Geneva: World Health Organization, available at https://extranet.who.int.
Bhatt, D. et al., Transitional hypothermia in preterm newborns. J Perinatol Journal of Perinatology, 27, 45-47. doi:10.1038, (c) 2007.
Liang, L. et al., Portable Infant Warmer, Dec. 13, 2010, available at www.who.int.
Abhat, A., Low Temperature Latent Heat Thermal Energy Storage: Heat Storage Materials, 1983, Solar Energy, vol. 30, Issue No. 4, pp. 313-332.

* cited by examiner

APPARATUS AND METHOD FOR MAINTAINING ENTHALPY WITH SECONDARY MECHANISMS

RELATED APPLICATION DATA

This application claims priority of U.S. Provisional Application No. 62/288,480 filed on Jan. 29, 2016, which is incorporated herein by reference in its entirety.

TECHNICAL FIELD

The present invention relates to an apparatus and method for providing warming therapy for newborn babies in remote areas and developing countries. More specifically, the invention relates to an interactive enthalpy exchange system between primary and secondary heat sources and the patient, all being ambient sensitive

BACKGROUND

Roughly 15 million infants are born premature every year. Prematurity is a daunting challenge we face all over the world, despite advances in healthcare. Due to the lack of standardized healthcare infrastructure available for the pregnant mother and newborn infant, prematurity is more prevalent in rural areas and developing countries. With a disproportionately large body surface and little subcutaneous fat with respect to the total body weight, newborns, especially a majority of the low birth weight infants (LBW<2.5 Kg) and very low birth weight infants (VLBW<1.5 Kg), are at higher risk for hypothermia. Hypothermia is defined as the consequence when total heat loss exceeds an infant's ability to generate heat and maintain normothermia.

According to the World Health Organization (WHO), a newborn with a temperature of 36.0-36.4° C. is under cold stress (mild hypothermia), which should give rise to concern; 32.0-35.9° C. is in danger and must be warmed right away (moderate hypothermia), and <32° C. has a grave outlook with urgently required skilled care (severe hypothermia). Prolonged hypothermia is linked to impaired growth with increased neurological deficits, increased vulnerability to infections (e.g., sepsis), and negative effects on auto-immune functions, all leading to increasing infant morbidity and mortality rates in the world. Helping to maintain normothermia of a newborn infant's first few days of life is important to long-term sustenance and a reduction of morbidity rates overall. Fragile LBW and VLBW premature infants are susceptible to deleterious injuries, as a result of repeated handling and constant movement. It is best to maintain a stable, warm environment in the first few days of life until the infant is able to regulate its body temperature or until the infant is in the hands of trained caregivers in nearby dispensaries/hospitals, where standardized care can be accessed.

Thermal stability is important for survival of premature LBW and VLBW newborn infants. Although body heat is lost in four ways (conduction, convection, radiation and evaporation), normothermia can be attained with external sources. Thermal stability can be achieved indirectly via forced air warming in incubators, directly via radiation with radiant warmers (e.g., remote heating with heat lamps etc.) and through a reduction in evaporation by wrapping the infant with a thermal insulator (e.g., plastic wrap etc.) to preserve humidity. Indirect and remote heating methodologies used in complex stationary/transport incubators and radiant warmers readily available in advanced countries require high power (up to 2 A at 240 VAC is roughly 480 watts 500 W) and are very expensive ($25,000-150,000). They are unfit for use in remote locations in developing countries as they require continuous power and rigorous cleaning. Due to the presence of airborne pathogens as a result of closed-loop warming, thorough disinfection with harsh industry chemical agents is essential for incubators, a lack of which can give rise to cross-contamination between patients. For these reasons, incubators are not accepted as a standard of care in most developing countries. Radiant warmers currently accepted are unsuitable for transport and cannot be used outside of the hospital setting.

U.S. Pat. No. 7,934,537 B2, May 3, 2011 to Kolowich discloses the use of a thermally equalizing phase change material intended to first bring down a hot beverage temperature by heat absorption followed by releasing thermal energy back from the phase change material stacked between an inner and outer receptacle to the beverage to help maintain it in a warm state for an extended period.

A transwarmer disclosed in U.S. Pat. No. 5,058,563, to Manker et al. discloses the use of an inorganic, salt-based warming gel to support infant transport and radiology exams for up to 2 hours. This is not economical and therefore unreasonable for maintaining normothermia in the first few days of life.

U.S. Pat. No. 8,257,417 B2, Sep. 4, 2012 to Chen et al. takes this concept a bit further with the use of organic based phase change material mattress that can be used roughly 50 cycles for up to 4 hours per use. U.S. Pat. No. 8,834,548 B2, Sep. 16, 2014 to Liang et al. provides a suitcase shaped warmer for this phase change material mattress based on water heating or electric heating for reuse. This was followed by US patent application no. US2015/0066119 A1, Mar. 5, 2015 of Panicker et al. which discloses monitoring patient temperature with an electronic display with integrated visual alarms prompting user intervention.

In general, every incubator/warmer manufacturer has some kind of monitoring equipment built-in to their device. The phase change material (PCM) works well when the temperature is elevated to above the solid-liquid transition temperature, however the PCM becomes very solid below this transition temperature as the material cools off rapidly. Hypothermia induced as a result of removing heat in the first few days of the fragile infant can be dangerous. Repeated handling to change the mattress every few hours can also be harmful to the infant.

SUMMARY OF THE INVENTION

A practical, transportable, battery powered infant warming strategy that is adjustable to ambient surroundings is described. The device in accordance with the invention provides instant warmth to an infant and can be economically used in remote areas and in developing countries.

The device in accordance with the invention highlights advancements with patient warming for a period of 1-2 days, while also obviating the need for repetitive handling of fragile infants. A primary heat source may be used with moderate to high latent heat capacity, capable of providing warmth for up to 4 hours that can be extended to a period of two days with an efficient, safe, secondary warming medium. Efficiency may be maintained by presenting the user a means of controlling secondary heat based on the patient temperature, embedded environment and ambient surroundings.

The device in accordance with the invention can utilize an interactive enthalpy exchange system between primary and secondary sources including the patient, all being ambient sensitive, i.e., responsive to temperature changes of the primary material, secondary heat source, the patient, and environment during transport until the patient is transferred to a stable clinic or hospital environment. The secondary heat source can be composed of either a rigid or flexible printed circuit board-based resistive network that can be powered with a rechargeable, portable battery.

High-efficiency conductive, gel-based heating (i.e., direct heat transfer via conduction) may be possible during infant transport with specialized mattresses. These one-time use mattresses maintain 40° C. on their surface where the infant is placed for a period of up to 2 hours. Repetitive use of up to 50 times and prolonged heating period of up to 4 hours is possible with the use of PCM-based warmer. Repeated use of the mattress is possible by re-warming the mattress to exhibit a phase change from solid to liquid, either by immersion in boiling water or by electric heating. A disadvantage of this PCM mattress is of its single fault design, i.e., as the phase changes, the material becomes solid, and thus, quite uncomfortable for the infant.

The present disclosure is intended to eliminate hypothermia by providing a means of enthalpy exchange between the energy sources (primary, secondary heat sources, and the patient). The secondary heat source is capable of maintaining normothermia by using baseline power, which is highly efficient. This baseline power can be generated via a self-regulating, printed circuit board-based resident matrix heater, embedded within a warm primary heat source (e.g., within a gel or PCM mattress) and powered by a battery such as a widely available car battery. In doing so, a further intention is to virtually eliminate the need to remove the infant from the "kangaroo pouch" during the first days of his or her life thereby minimizing additional risks associated with disturbing fragile infants and improving patient safety.

The present disclosure is novel in that heat provision to the infant may be sustained in-situ for an extended period, through the efficient use of a secondary mechanism for warming a primary medium and maintaining normothermia with respect to the ambient surroundings. Also novel is monitoring of the temperatures of the patient and others (primary, secondary sources, and ambient environment) including available battery power, leading to smarter algorithms and simple, easy-to-use instructions with audio/visual alarms. Ambient noise disturbances from surroundings and from the alarms generated by the electronics can be reduced with the help of noise attenuating foam pads over the infant's ears.

The primary material can be composed of organic, inorganic, hygroscopic, clay based materials or combination thereof. The gel or phase change material-based primary medium should have an optimum circuit dependent on the heat capacity of the primary source, the available input power and the time required to maintain secondary heating based on the ambient environment. By maintaining minimum or baseline heating of the primary heat source, the need for maximum heater power for the secondary heat source over extended periods may not be necessary, thereby making the system highly efficient. In addition, providing minimal heating may also eliminate wide enthalpy fluctuations seen with the gel/PCM mattress alone as they transition through the warm and cold stages.

Under the present disclosure, minimum enthalpy exchange is anticipated between the patient, primary medium and secondary network, considering the ambient environment with little or no thermal cycling, which, in turn, results in uniform infant warming. One or more novel embodiments operating between 10-50 W, with the use of up to two 12V batteries intended to provide uninterrupted heat for 20-24 hours is discussed. It should also be evident to one skilled in the art of accomplishing enthalpy exchange using heating mechanisms outside the gel/PCM mattress or combination thereof. Secondary heating mechanisms other than use of resistive networks, for example, such as with thermoelectric networks, is possible. With such mechanisms, cooling is also possible. Clearly, the benefits of maintaining normothermia in the first few days of infant life and reducing infant handling is necessary in remote areas of developing countries until standardized healthcare is accessed. The need for a simpler, more practical infant warming therapy in the first few days of life is now apparent.

The device in accordance with the invention provides safe warming therapy to infants in the first few days of life, through an interactive enthalpy exchange between primary and secondary heat sources, in combination with the patient. System power consumption is optimized in accordance with the ambient environment for a period of 1-2 days, through the use of a fully charged battery, such as a widely-available car battery.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

DEFINITIONS

The term infant (from the Latin word for infans, meaning unable to speak or speechless) relates to a newborn infant, premature or otherwise, and small babies generally from birth up to one year of age.

The term transport relates to safely moving the infant patient with all of his or her life sustaining equipment and monitoring tools from remote areas to a standardized healthcare setting The term enthalpy is a thermodynamic state function. It is used here to simplify energy transfer between systems; the patient, primary and secondary heating sources, and the environment. The total enthalpy, H, of a system cannot be measured directly, only the change in enthalpy, $\Delta H$. The $\Delta H$ is a positive change in endothermic reactions, and negative in heat-releasing exothermic processes.

The phrase enthalpy of fusion also known as (latent) heat of fusion (or thermal heat capacity) refers to the change in enthalpy resulting from heating a given quantity of a substance to change its state from a solid to a liquid. The temperature at which this occurs is the melting point. Thermal heat capacity depends on the amount of material and is specified in joules/gram (SI unit).

The phrase modular system relates to an interactive enthalpy exchange system assembled with individual components such as a kangaroo pouch, a battery holding transporter, a user interactive control/display unit, the system capable of being quickly assembled or disassembled for ease of installation, de-installation, service, trouble shooting, satisfy design constraints, usability etc.

DETAILED DESCRIPTION

The present disclosure enhances infant comfort with a mattress (e.g., gel-based mattress). By providing the means for secondary warming via a self-regulating, battery powered, resident matrix heater embedded within the warm gel mattress, the need to move the infant from a "kangaroo pouch" during the first days of the infant's life is virtually eliminated.

The aim of the present disclosure is to sustain heat provision to the infant in situ for an extended period, with an additive, secondary heat source embedded within the already warm gel mattress, the secondary heat source capable of heat provision on its own. By maintaining minimum or baseline heating of the gel based substrate, the need for maximum heater power over extended periods can be eliminated, thereby making the system more efficient. In addition, providing minimal heating may also eliminate the temperature fluctuations of the substrate, and therefore, stabilize heat provided to the infant. The preferred embodiments of the present disclosure describe the use of 10 W-50 W resistive matrix heating power, embedded in a gel-based inorganic or organic substrate mattress and powered by one or more 12V batteries, as to provide uninterrupted heat for 1-2 days in controlled environment settings of 20° C., 25° C. and 30° C., respectively. Sensor dependent and independent feedback is used in several places to improve performance, safety and effectiveness of the device. Software-independent hardware measures are incorporated to minimize risk while enhancing patient, operator and equipment safety. Operator visual and audio alarms are incorporated to regulate power based on the temperatures of the patient, primary and secondary heating sources and the environment and the available battery power. Recharging of the batteries is possible with widely-available, routine means available everywhere.

Figure 1:
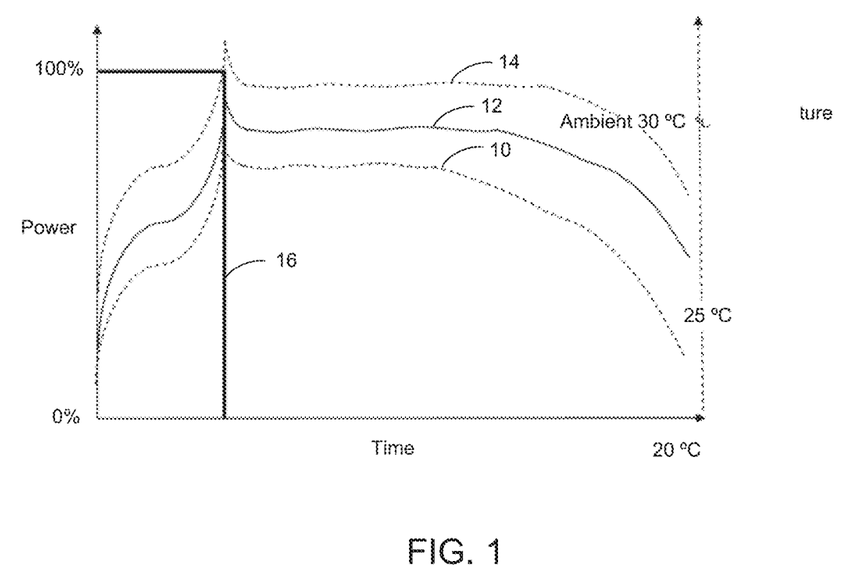
FIG. 1 is a graphical representation of the power for heating a phase change material (PCM), including its temperature behavior illustrating heat retention capacity suitable for warming the infant at different ambient temperatures

Referring initially to FIG. 1, shown is a graphical representation of the typical amount of supply power for heating a gel/phase change material, including the temperature characteristics 10, 12, 14 of the chosen gel/phase change material, illustrating its heat retention capacity suitable for warming the infant at different ambient temperatures. The solid-dark line 16 shows when the power is ON to heat the gel/phase change material. Once the gel/phase change material crosses the set temperature, the heat is turned OFF. With this transient change in power, it takes a few minutes for the gel/phase change material to stabilize its enthalpy. Then, steady state is maintained for a few hours depending on the properties of the gel/phase change material including its heat retention capacity and exchange with the subject. Primary heat sources with heat storage capacity of 100 J/g (joules/gram), typically around 200 J/g are preferred, whereas phase transition temperatures of anywhere from 30-46° C. are desired.

After a few hours, as enthalpy difference with the subject increases, temperature of the gel/phase change material of the primary heat source drops as it loses heat. Temperature drop of the gel/phase change material below the patient skin temperature of 37° C. can be detrimental to the infant. That is, instead of keeping the infant warm, the body heat from the infant may be drawn away, which can lead to hypothermia if left untreated. This is exacerbated at the low ambient temperatures, for e.g., 20° C. Here, it takes longer to maintain the liquid phase of the phase change material; the shorter the meaningful enthalpy exchange, the more drastic is the cooling off of the primary heat source, rendering the thermal conditions highly undesirable for the infant. At higher ambient temperatures, e.g., 30° C., the effect is quite the opposite; i.e., the quicker it is to go past transition temperatures, the longer the heat retention and the slower the temperature drop off. Thus, a controlled mechanism is needed to maintain normothermia for the infant, based on the ambient environment temperature.

Figure 2:
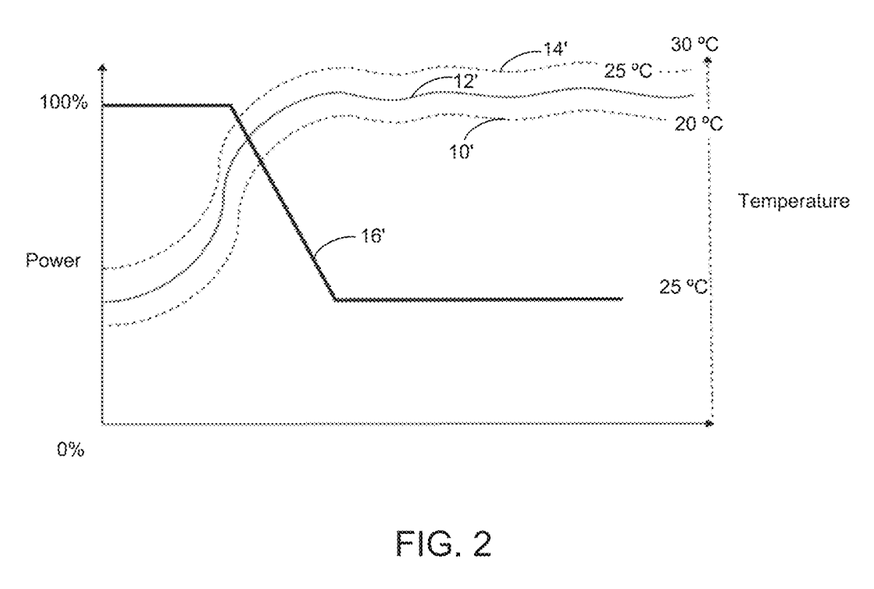
FIG. 2 is a graphical representation of power for maintaining operator set temperature for an infant incubator or infant warmer at different ambient temperatures.

Moving to FIG. 2, shown is a graphical representation of the power expended to maintain operator-set temperature and heat-rise curves 10', 12', 14' for an expensive infant incubator or an inefficient, commercially available infant warmer at different ambient temperatures (20° C., 25° C. and 30° C.). Temperature heat-rise curves illustrate damped oscillations to reach equilibrium, whereas typical power curves 16' to reach operator-set temperature are shown to illustrate different phases; during warmup and steady-state, respectively, at 25° C. As temperature rises to operator set values, power lowers from 100% to whatever is necessary to maintain steady-state at the operator-set temperature. Algorithms and electronics are employed based on feedback control theory. Once the power is lost, cooling begins immediately. These incubators and warmer devices need high power for operation (of the order of 300-500 W) and require rigorous cleaning/disinfection procedures to eliminate cross-contamination between the patients who reside in them for up to 1 month. These devices are not suitable for use in remote areas and are not suitable for transport.

Figure 3:
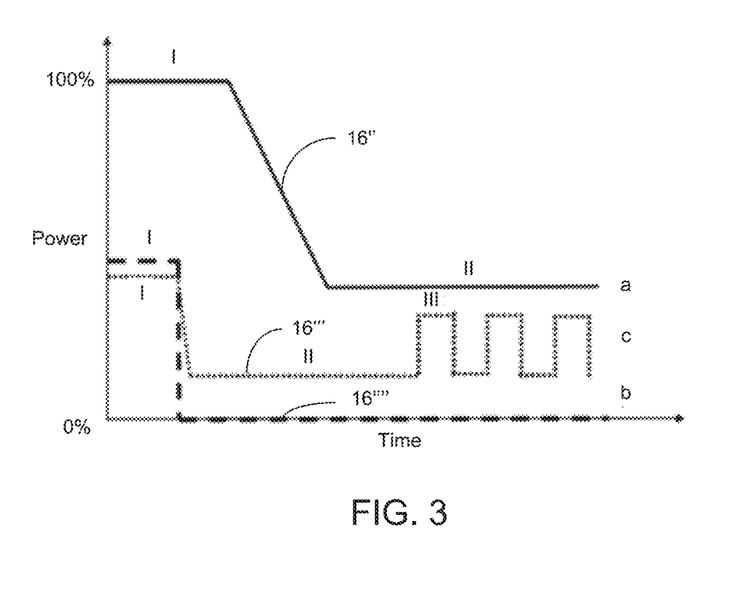
FIG. 3 is a simplified graph of power versus time required by expensive commercial incubator/warmer (a), to heat a given phase change material (b) and proposed invention using feedback mechanisms to optimize power at a given ambient temperature (a, c).

FIG. 3 shows simplified power graphs of the power supply to an interactive enthalpy exchange system in accordance with the present disclosure, representing amount of power for heating a gel/phase change material of the primary heat source past its transition temperature (a), to show power expended in a conventional incubator/warmer (b), and to highlight current application of the battery operated, primary-secondary supportive, enthalpy-maintaining mechanism (c). With reference to the gel/phase change material based warming (a), either the power is ON to warm the material or OFF resulting in a single heating phase. With respect to the bi-phasic heating cycle of a conventional incubator/warmer (b), heating begins with full power at start which reduces gradually as temperature rises and approaches steady-state. Algorithms based on feedback control from sensors regulate power to maintain steady-state over an extended period.

Transition rate from state I to state II depends on the size of the incubator/warmer, heater size, temperature setting and air flow pattern. Very small variations computed by algorithms based on feedback sensors are expected in state II to maintain steady-state. With continued reference to FIG. 3 (c), multi-phase heating with maximum power in the beginning, followed by deregulation of power, then cycling is anticipated to maintain steady-state for an extended period. Maximum power in the beginning (Phase I) helps transition the gel/phase change material of the primary heat source, i.e., inherit enthalpy, whereas transition from I to II will help maintain enthalpy over an extended period (Phase II) followed by cycling (Phase III), if necessary, to retain enthalpy of the system necessary and provide consistent warmth to the infant.

The concept is clear: maximum power (state I) allows heating of the primary heat source, so enthalpy of the system can be maintained for a few hours. The primary heat source can be heated two ways by utilizing maximum power from ambient cold state to arrive at the set temperature:

a) independently by dipping in a hot water bath, or by placing between parallel heater plates etc. or by any other means (air convection, optical, etc.) or their combination OR b) the secondary heat source.

Alternately, a combination can be utilized.

State I indicates maximum power provided to the primary heat source (gel/phase change material) via an independent means or by the secondary heat source or their combination to arrive at or near the set temperature from ambient cold (resting) state. Since greater amounts of enthalpy has to be transferred to the system at the ambient, resting ground state, the power needed in Phase I can be maximum of the three states (I-III).

The reduced power state II assists to maintain enthalpy as the heat capacity of the primary heat source begins to vane. State III regulates power efficiently, one way by cycling as the gel/phase change material approaches the transition temperatures, to ensure the overall system enthalpy is maintained. In addition, states II and III extend power to withstand changes in the ambient environment and adapt to infant body temperatures. Amplitudes of state II and III and the cycling of state III (time ON versus OFF) can be manually set by carefully designing the secondary resistive networks so that their impedance is altered to support warming over an extended period (e.g., 1-2 days). In addition, instructive audio and visual alarms allow the user/operator to dial switches per concepts shared in FIGS. 4A-B, and 8, 9, to permit alteration of states II and III.

Figure 4A:
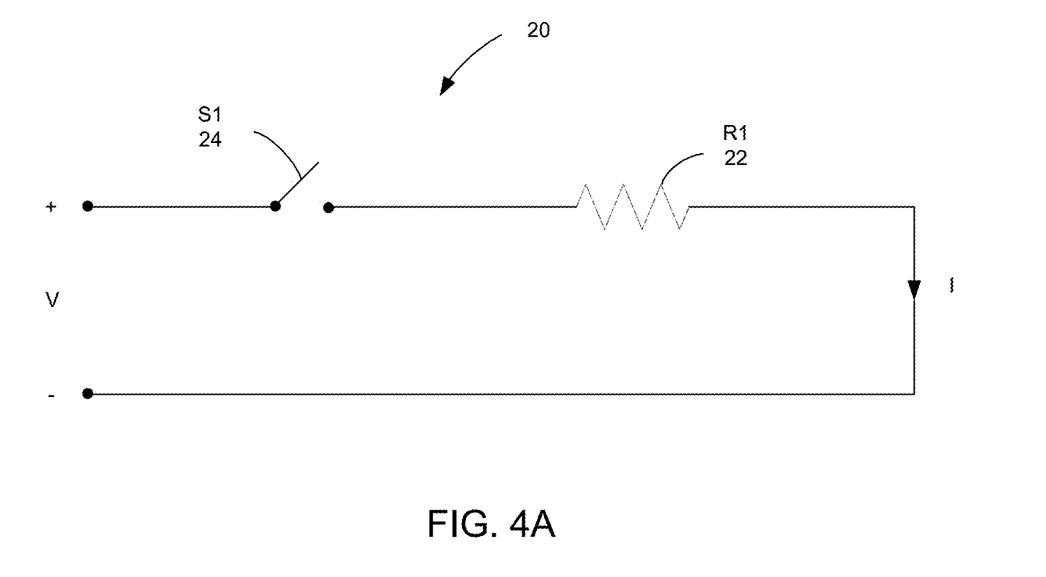
FIG. 4A represents a simple secondary network for adjusting power supply to an interactive enthalpy exchange system.
Figure 4B:
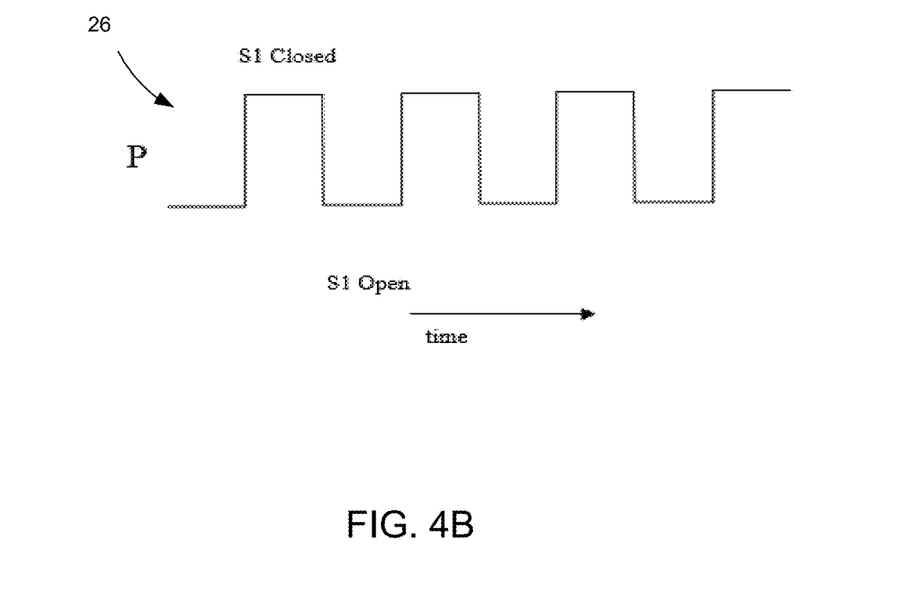
FIG. 4B shows a pulse cycle of the power supply via the secondary network of FIG. 4A.

FIG. 4A is a simple representation of adjusting power supply level, by a secondary network 20 which varies voltage/current to a load resistor R1 for a voltage input V and current I, with a manual or electronic switch S1. FIG. 4B represents a pulse cycle 26 of the power supply to the secondary network 20 of FIG. 4A. A closed switch S1 allows current to pass through the resistor R1, and thus, generates power ($P=I^2R1$). With the switch S1 open in the secondary network 20, there is no current across the resistor R1, and thus, resulting in zero power. The power expended by the secondary network 20 may help to generate or maintain the gel/phase change material of the primary heat source above the transition temperature which, in turn, provides warmth to the infant.

Figure 5A:
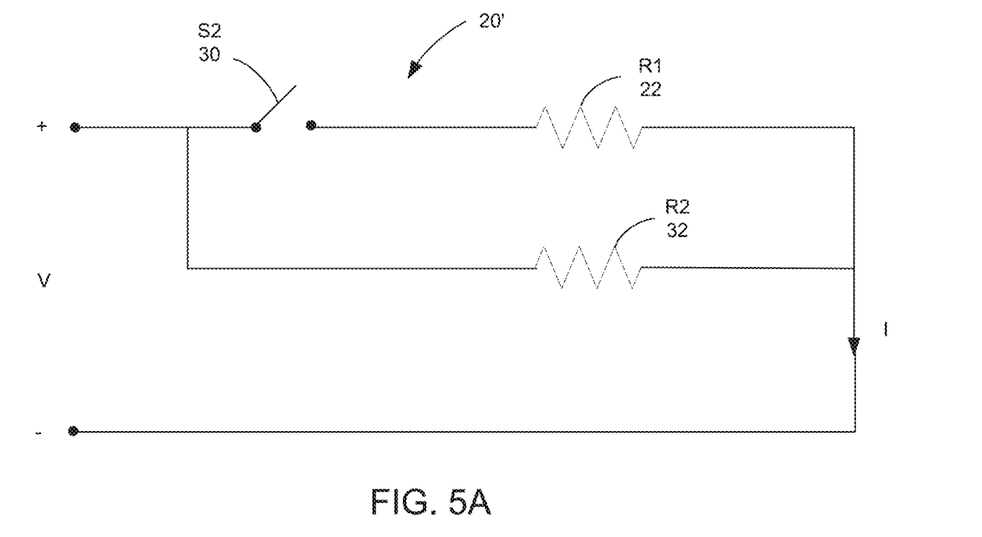
FIG. 5A shows another secondary network for adjusting power supply to the interactive enthalpy exchange system in accordance with the present disclosure.
Figure 5B:
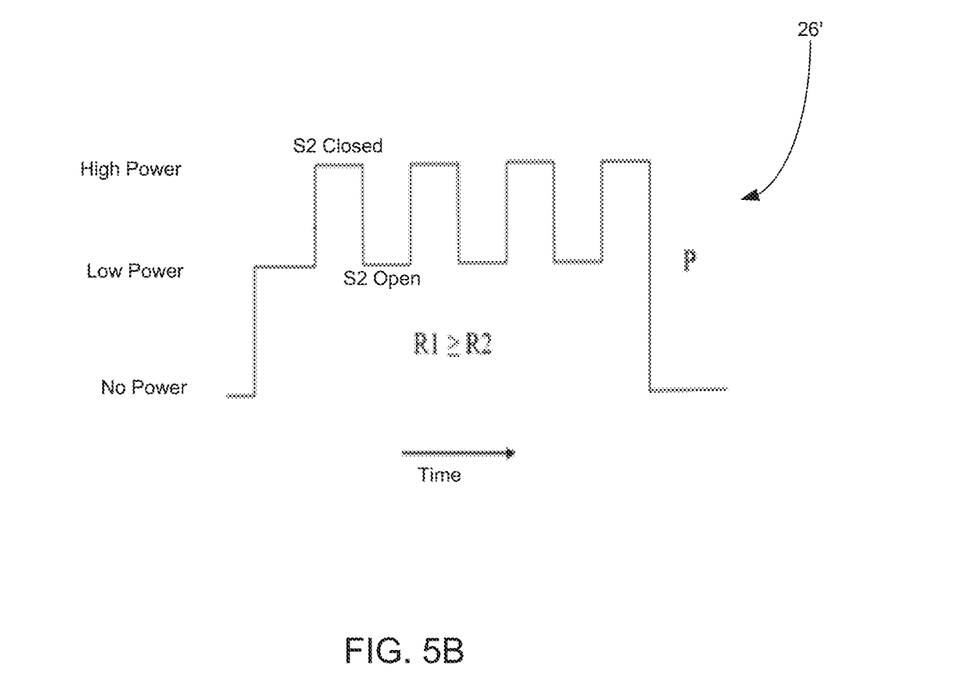
FIG. 5B represents a pulse cycle of the power supply via the secondary network of FIG. 5A.

FIG. 5A is another simple embodiment of the pulse cycling approach of FIGS. 4A-B with the secondary network 20' having two load resistors (R1, R2) for a voltage input V and total current I. An open switch S2 allows current to pass through a second resistor R2, forcing the secondary network 20' to provide low power to the interactive enthalpy exchange system. With the switch S2 closed, current divides through the resistors R1 and R2. Specifically, where the resistors R1 and R2 are connected in parallel and resistance value of the first resistor R1 is greater than or equal to the resistance value of the second resistor R2 but less than or equal to five times of the resistance value of the second resistor R2, it results in overall reduced resistance, which, in turn, allows more current to flow, and therefore, generates higher power than having the second resistor R2 alone as in FIG. 4A. Likewise, when the resistance value of first resistor R1 is equal to the resistance value of the second resistor R2, the secondary network 20' will result in twice the power. When the resistance value of first resistor R1 is less than or equal to the resistance value of the second resistor R2, the secondary network 20' can generate other powers accordingly. Deviation of the combined R1-R2 resistance from the second resistor R2 alone as in FIG. 4A will determine the difference between low and high power supplies (low power=$I^2R2$, high power=$I_1^2R_1+I_2^2R_2$; $I=I_1+I_2$) generated as a result. A simple parallel combination with one switch, S2, in series with the first resistor R1 is shown in FIG. 5A. However, other combinations are possible (e.g., a series-parallel combination). FIG. 5B shows for power amplitude alteration 26' along with cycling using the secondary network 20' of FIG. 5A. Power curve shows by altering the position of the S2 switch, different power levels (low, high) can be achieved since the resistance of the system will be altered. With S2 closed, R1 is in parallel with R2. With S2 open, R1 is out of the circuit and the total resistance of the system is altered. In the former case, current is shared by R1 and R2, whereas in the latter case, current flows solely through R2. Without cycling, there can be only two power stages (low, high) with 100% duty cycle which can lead to over-heating and inefficient use of the available battery power. Power cycling at any level can be accomplished by altering the load with the use of simple timer circuits (e.g., timer circuit for aquariums that work on AC), at lower DC voltages anywhere between 6-24 VDC. A careful manipulation of both amplitude alteration and cycling will permit an efficient use of the available battery power needed to provide energy to the primary/secondary system, and thus, maintain enthalpy in the interactive enthalpy exchange system 40. This will, in turn, prolong or sustain infant warmth over an extended period.

Figure 6:
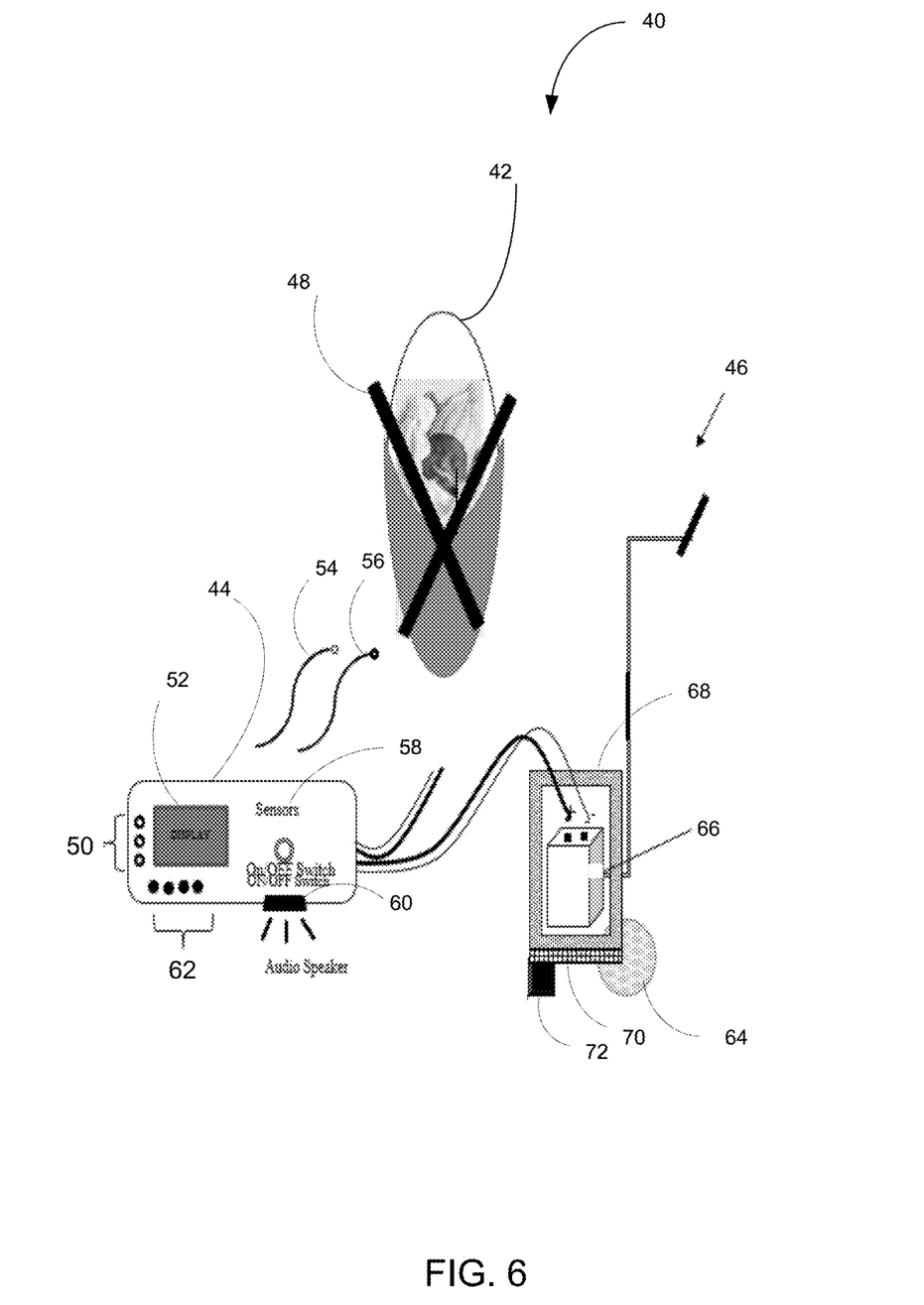
FIG. 6 shows a preferred embodiment of the interactive enthalpy exchange system with an infant patient placed within a pouch in accordance with the present disclosure.

FIG. 6 describes a preferred embodiment of a system in accordance with the invention. The modular system 40 includes three sections: a "kangaroo" pouch 42, a control/ display unit 44 and a battery holding transporter 46. The "kangaroo" pouch 42 and restraining mechanism (e.g. straps 48) may be designed for stationary use or transport care. "X" shaped straps 48 that go around the entire package can be used to carry the infant or attach to a transport means. Not shown are the combined primary/secondary heat module and pocket for holding the same which are discussed later with respect to the pouch sectional view in FIG. 7. Further details of the pouch 42 are not discussed here, but it is left to the reader to surmise a form fit solution to ensure maximum contact with the warming medium of the primary heat source and less exposure of the torso to ambient, with full access to the face/mouth for feeding and complete visual. A cap may be used to cover the head of the infant and the pouch 42 may cover the head to prevent heat loss. Ear plugs (not shown) of sorts may be used to reduce ambient noise disturbance to the infant.

The control/display unit 44 may be water-tight, rugged, portable, and user interactive. The control/display unit 44 includes a switch to turn on or off the interactive enthalpy exchange system 40 and LED lights 50 for indicating system status to the user. The control/display unit 44 may also include sensors 58 to sense temperatures. The control/display unit 44 may also include a display 52 for displaying temperatures of the patient, primary and/or secondary heating sources (discussed further later), and the ambient temperature. The control/display unit 44 may be normally attached to the pouch 42 and can be easily removed and attached to the battery holding transporter 46. Power and sensor cables 54, 56 can be merged into one for increased usability and maintain a simple design. The cable(s) 54, 56 can be removed or attached with a connector to the pouch 42 and the control/display unit 44. Likewise, a detachable power cable can be used between the battery holding transporter 46 and the control/display unit. The control/display unit 44 has means of communication with the user by way of audio/visual alarms (e.g., audio speaker 60), control knobs 62 and bright LED lights 50. A service 15 connection behind (not shown) allows debugging and software upgrade functions to be performed efficiently without the need to open the control/display unit 44.

Only a side view of the battery-holding assembly 46 is shown. The battery-holding transporter 46 may have wheels 64 (e.g., plastic or rubber wheels) as a transporting mechanism. The battery holding transporter 46 may be designed like an oxygen tank holder and may house batteries (e.g., car batteries 66) inside a battery enclosure 68. The battery enclosure 68 may be fire-proof, water-tight, and of plastic material with very high dielectric, so as to ensure safety during rain, lightning, in high static areas and at low temperatures with very low humidity levels (e.g., <20% rH). Flame rated batteries may be used. Batteries 66 may be held so there is no motion inside the battery enclosure 68. A battery charging plug/cable (not shown) may be provided, so that the batteries 66 can be charged by an external charger without having to remove the batteries 66. Inline charging and thermal fuses can be employed in the design for safety. The battery enclosure 68 may be placed on top a vibration dampener 70 to smooth the vibrations otherwise felt by the batteries 66 during motion. Likewise, during stationary use a rubber stopper 72 can serve as a vibration dampener 70 and for improved stability.

Figure 7:
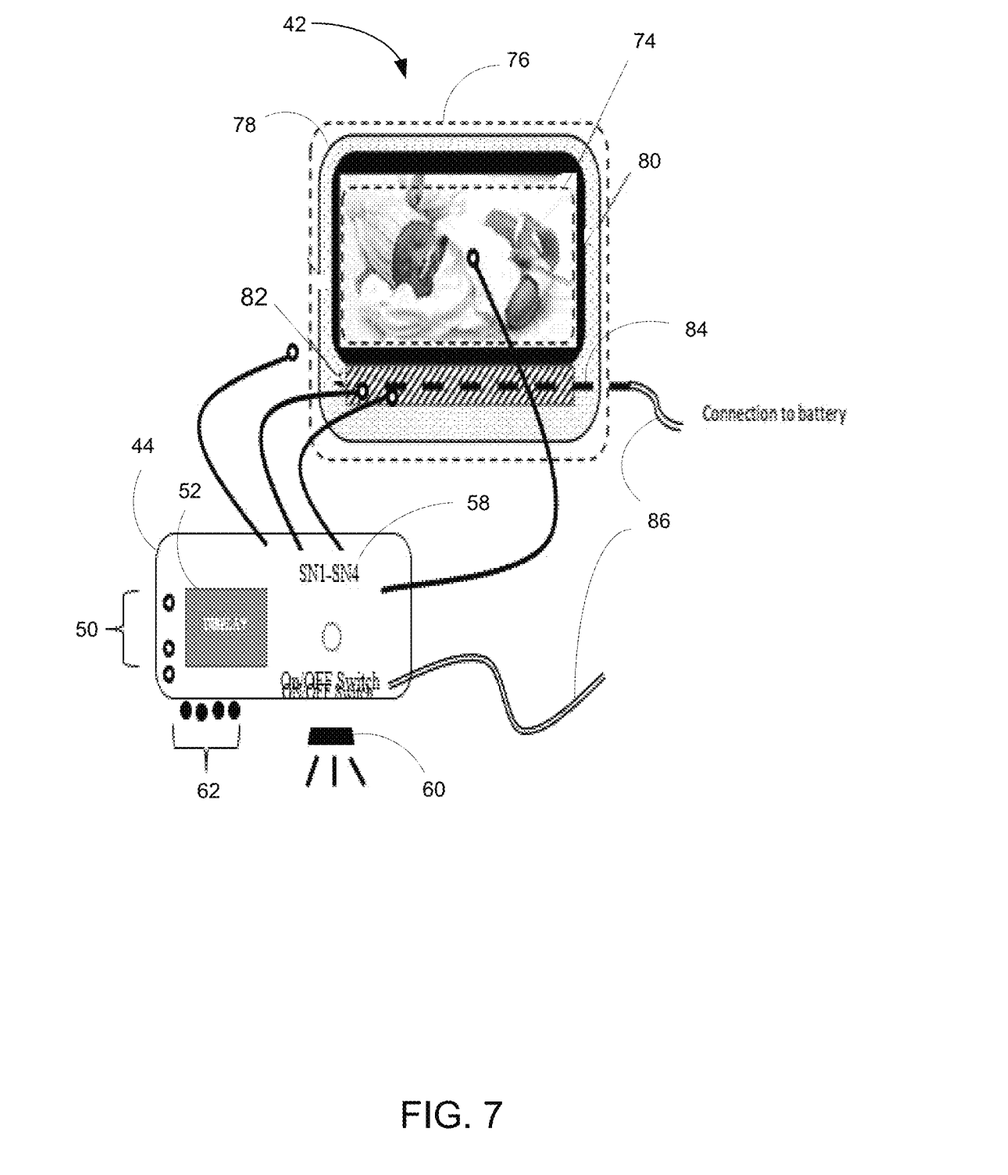
FIG. 7 is an infant holding sectional schematic of a control/display unit, an efficient warming cocoon showing all layers—covers, foam cushion, primary, secondary heat sources and connection to a battery of the interactive enthalpy exchange system of FIG. 6 in accordance with the present disclosure.

FIG. 7 shows a sectional view of an infant patient wrapped in the pouch 42 connected to the control/display unit 44, showing layers of the pouch 42—inner cover 74, outer cover 76, temperature insulator 78, foam cushion 80, primary heating source (e.g., PCM/Gel Material 82), secondary heating source (e.g., secondary resistive heating 84) and connection 86 to battery 66. The pouch 42 may be of a "kangaroo style" wrap made from polyethylene or nylon or polystyrene plastic material capable of withstanding a wide temperature range (e.g., −20° C. to 90° C.). The pouch is easy to disinfect through the use of local agents and can be held with Velcro straps to completely encompass the infant without covering the face, as to allow for direct visualization and feeding (not shown). The outer polyethylene layer, with a low temperature coefficient (k<0.25 BTU-in/hr-ft$^2$-° F.), also functions as a temperature insulator which is intended to maintain the heat within the infant wrap pouch 42 and insulate it from the external environment. This is also to ensure that the temperature of the inner cover 74 does not exceed 40-42° C., prohibiting overheating from outside the wrap sources of heat (i.e. direct exposure to sun light, proximity to a heater or stove etc.). The foam cushion 80 forms an inner, protective cushion support for the infant. The gel/phase change material of the primary heat source 82 and secondary resistive heat source 84 are encompassed in the pouch 42, which may be removable for possible replacement below the infant. It is preferred that the gel medium of the primary heat source 82 has a heat retention capacity (or latent heat of fusion, or thermal storage capacity etc.) of roughly 200 J/g. Higher values are preferred but normally come with additional restraints such as higher powers needed for phase transition etc. Likewise, a choice of organic, inorganic, eutectic salts, hygroscopic materials are also important to ensure optimum performance of the interactive enthalpy exchange system 40. For example, chemically stable properties such as the high heat of fusion, the ability to melt congruently, and safe and non-reactive behavior are the preferred characteristics of organic material. However, the low thermal conductivity and low volumetric latent heat storage capacity in their solid states require high heat transfer rates. This is avoided in the current application during use of the novel secondary heat source, concepts and circuits discussed in FIGS. 4, 5, 8, and 9, respectively. In addition, care should be taken to insulate the electronics, so as to avoid the embedded secondary resistive heater matrix come in direct contact with the gel/phase change material of the primary heat source 82 and cause a short-circuit. Short circuits alter circuit impedance, current patterns, the overall battery power expended and can result in hot spots. Insulation can be accomplished with the use of high temperature epoxy glues that are flexible. In addition, inline current limiting and thermal fuses can be employed to mitigate adverse events.

Connections to the battery 66, sensor locations and the audio/visual alarm display panel 52 for user interface are all partially shown. Sensors SN1-SN4 58, obtain temperatures of the infant, primary heat source 82, secondary heat source 84 and ambient environment for feedback. Low and high temperatures past a pre-set chosen window for safe operation including low-battery state trigger audio/visual alarms, which prompt the user to take future course of action. Sensing and feedback circuitry can be analog, digital or their combination. The secondary heat source 84 can be resistor based or via other means (e.g., thermoelectric circuits). Compact piezoelectric speakers with high audible alarms in the range of 80-100 dBA are preferred, audio alarms can be paused for a brief time period depending on fault priority (low, medium or high). Visual alarms may be LED or LCD based or their combination. Audio alarms may be via beeping based on (low, medium, high) priority and or in local language for user interaction.

Figure 8:
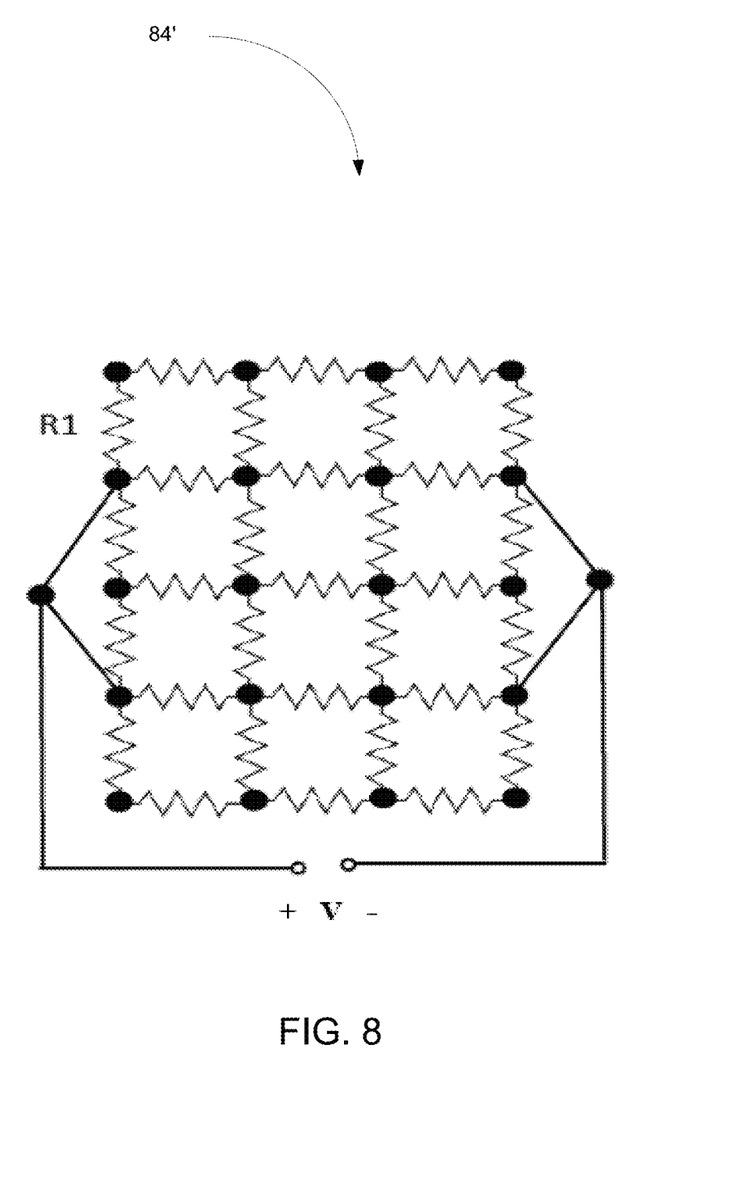
FIG. 8 shows an embodiment of a secondary resistive heating circuit that spans the surface area encompassed by the medium of the primary heat source in accordance with the present disclosure.

FIG. 8 shows one embodiment of the exemplary secondary heat source 84' employed in this application that overlaps completely, and partially spans the surface area occupied by the gel/phase change material of the primary heat source 82. This thirty-one count resistor (R1) network 84' is driven symmetrically in two places per lead connection which are connected to the battery +/− terminals via the electronics and display (not shown). The idea of the two-fold symmetrical connection is to normalize the current in every rung. This results in a uniform current distribution, and therefore, uniform heating based on the resistive heating explained above ($I^2R$) of the gel/phase change material of the primary heat source by absorbing sufficient thermal energy from the secondary heat source 84' to maintain its own enthalpy (endothermic reaction, $+\Delta H$), while releasing (exothermic reaction, $-\Delta H$) uniform heat to the infant.

Figure 9:
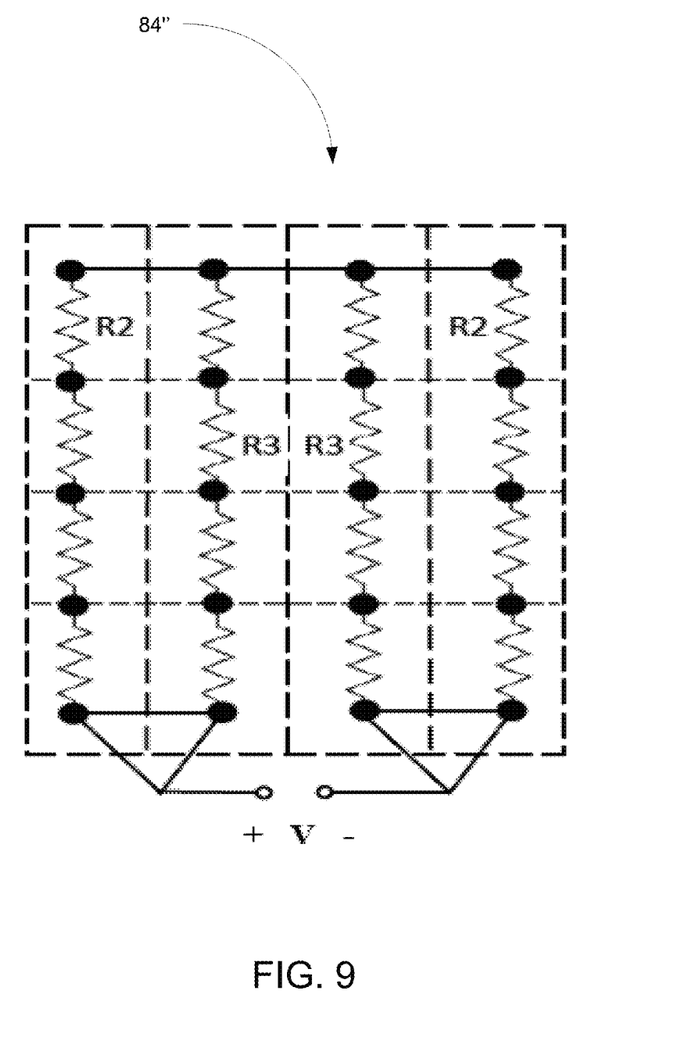
FIG. 9 is another embodiment of a secondary resistive heating circuit in accordance with the present disclosure.

FIG. 9 is another embodiment of the secondary heat source 84". This secondary sixteen resistor network 84" has a simple parallel-series connection which results in total resistance of 4R2 (resistance of one rung consisting of four R2 resistors in series) when the resistance values of R2 and R3 are equal. This allows for equal current distribution in all rungs, resulting in uniform heating of the secondary heat source 84" if each resistor (R2, R3) were physically placed equidistant from one another (in two-dimensions as shown). With R1=5Ω, R2=R3 and two 12 VDC batteries (I=1.2 A, P=28.8 W), the secondary sixteen resistor network 84" can reach 80-100° C. in 5 minutes in room air. When embedded in a gel/phase change material of the primary heat source, the maximum temperature can reach 40-50° C., sufficient to maintain the gel/phase change material of the primary heat source above its transition temperature. Heating of the gel/phase change material of the primary heat source 82 from its coldest state is gradual and can take up to 30 minutes, whereas maintaining enthalpy of the interactive enthalpy exchange system 40, once steady-state is reached, is much faster and very efficient, through the alteration of the power levels and cycling, concepts explained in FIGS. 4 and 5, respectively. By concomitantly reducing the battery voltage from 24V to 12V DC and total rung resistance to 10Ω, a less-bulky, 14.4 W system demanding careful choice of gel/phase change material of the primary heat source/secondary heat source and component values will be created. Batteries generally having 55-60 AH capacities should provide enough power for secondary heating for 1-2 days. Note that car batteries can be recharged to full capacity using a locally available low-cost charger.

In unique cases when non-uniform heating is required per physical design, demands of the infant mattress or that of the enclosure, is possible when R2≠R3. Unequal resistors result in different currents in the rungs, and therefore, intentionally, selective non-uniform heating pattern, targeting the region of interest. This sort of a selective, targeted heating pattern can be advantageous, for example, in instances where full heating of the gel/phase change material of the primary heat source 82 directly under the infant head is not desired. Total resistance of the secondary resistive network 84" of FIG. 9 can be 2(4R2||4R3). Based on these two secondary heating patterns, other variations can be practiced by those skilled in the art. The outer plastic covers 76 can be molded along with the gel/phase change material of the primary heat source 82 alongside the resistor networks with a connector for seamless insertion in to the "kangaroo pouch" 42.

Figure 10:
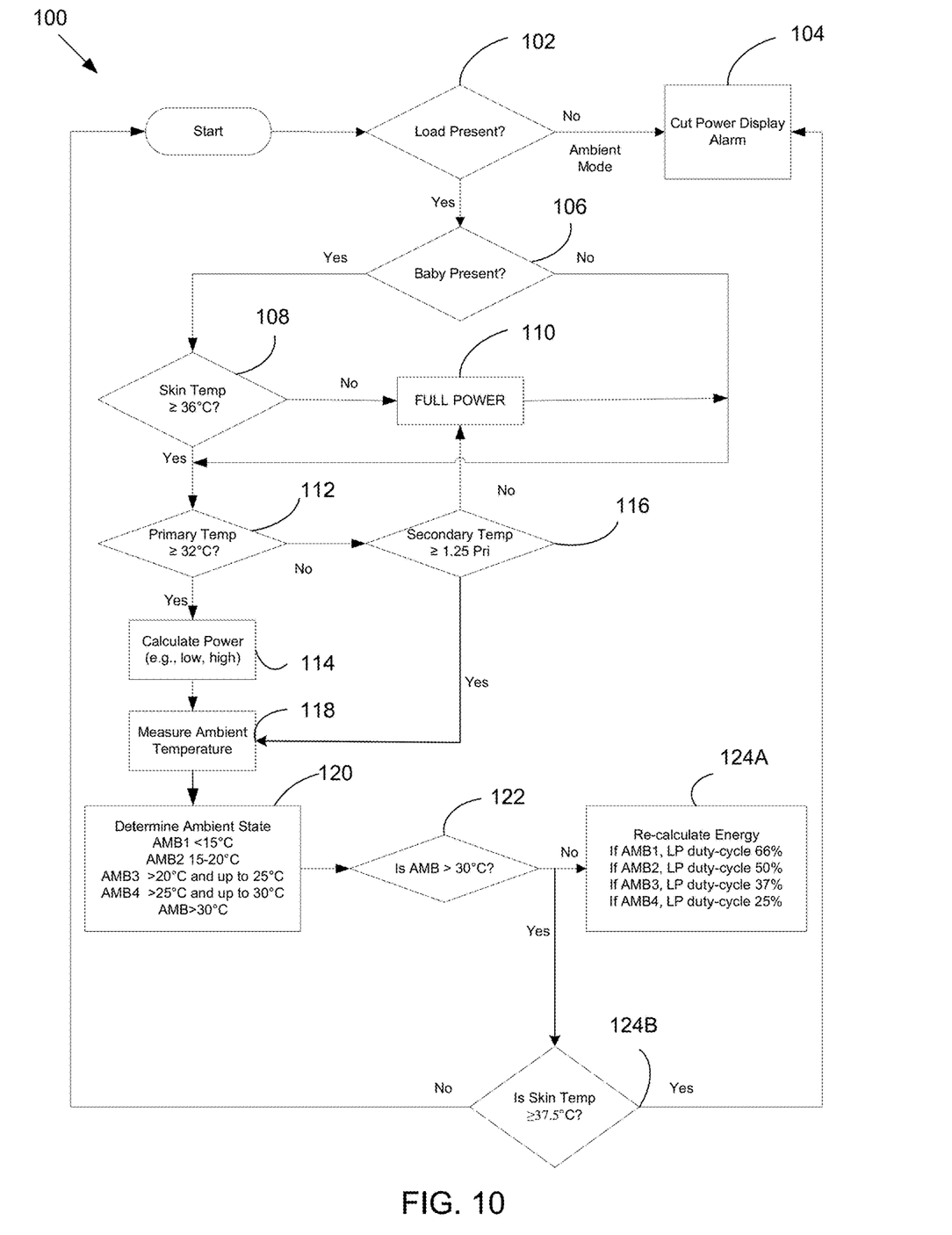
FIG. 10 is a flow chart illustrating exemplary steps that may be executed to maintain enthalpy by an interactive enthalpy exchange system between primary and secondary sources including the patient, all being ambient sensitive.

FIG. 10 illustrates exemplary steps that may be executed to maintain enthalpy by an interactive enthalpy exchange system 40 among primary heat source 82 (e.g., a gel/phase change material medium), secondary heat source 84 and the patient, all being ambient sensitive. The exemplary method 100 may be carried out by executing the steps via a processor and memory, where the logical operations are stored in the memory. Thus, the flow chart of FIG. 10 may be thought of as depicting steps of a method carried out by an electronic device, such as a controller or the like. Although FIG. 10 shows a specific order of executing functional logic blocks, the order of executing the blocks may be changed relative to the order shown. Also, two or more blocks shown in succession may be executed concurrently or with partial concurrence. Certain blocks also may be omitted. In addition, any number of functions, logical operations, commands, state variables, semaphores or messages may be added to the logical flow for purposes of enhanced utility, accounting, performance, measurement, troubleshooting, and the like. It is understood that all such variations are within the scope of the present invention.

Two modes of operation possible are heating and ambient modes. In the heating mode, sensor dependent and independent feedback are used in several places throughout the interactive enthalpy exchange system 40 to improve performance, safety and effectiveness of the system. In the ambient mode, power is deliberately cut but continued sensing is possible. The ambient mode is desired when no-heating is required or when over-heating continues to occur and user interaction is repeatedly necessary.

Beginning at step 102, it is determined whether a resistive load is present on the interactive enthalpy exchange system 40. If at step 102, it is determined that no resistive load is present in the interactive enthalpy exchange system 40, then the method moves to step 104. At step 104, power is removed and an alarm is displayed at the display unit (FIG. 7 (52)) of the control/display unit 44. However, at step 102 if a resistive load is determined to be present, then the method 100 moves to step 106. At step 106, it is determined whether an infant patient is also present in the modular system 40. If at step 106, the infant patient is determined to be present in the modular system 40, then the method moves to step 108. At step 108, it is determined whether the skin temperature of the infant patient is greater than or equal to 36° C. If it is determined that the skin temperature of the infant patient is not greater than or equal to 36° C., then the method moves to step 110. At step 110, the power supply to the modular system 40 is raised to the full level, and the method moves to step 112. If, at step 106, it is determined that the infant patient is not present in the modular system 40, then the method moves to step 112.

At step 112, it is determined whether the temperature of the gel/phase change material of the primary heat source 82 is greater than or equal to 32° C. If it is determined that the temperature of the gel/phase change material of the primary heat source 82 is greater than or equal to 32° C., then the method moves to step 114. At step 114, the power supply level to the modular system 40 is calculated and the method moves to step 118. If, however, at step 112 it is determined that the temperature of the gel/phase change material of the primary heat source 82 is not greater than or equal to 32° C., then the method moves to step 116. At step 116, it is determined whether the temperature of the secondary heat source 84 is greater than or equal to 1.25 times the temperature value of the gel/phase change material of the primary heat source 82. If it is determined that the temperature of the secondary heat source 84 is greater than or equal to 1.25 times the temperature value of the gel/phase change material of the primary heat source 82, then the method moves to step 118. If, however, it is determined that the temperature of the secondary heat source 84 is not greater than or equal to 1.25 times the temperature value of the gel/phase change material of the primary heat source 82, then the method moves to step 110 at which the power supply to the modular system 40 is raised to the full level, then the method moves to step 112.

Now, at step 118 the ambient temperature is measured and the method 100 proceeds to step 120. At step 120, the ambient state (AMB1 through AMB4) is determined from the measured ambient temperature. AMB1 indicates the measured ambient temperature is less than 15° C. AMB2 indicates the measured ambient temperature ranges from 15° C. to 20° C. AMB3 indicates the measured ambient temperature is greater than 20° C. and ranges up to 25° C. AMB4 indicates the measured ambient temperature is greater than 25° C. and ranges up to 30° C. As will be appreciated, the specified ambient states are exemplary, and different and/or additional temperature ranges can be used as required by the specific application. At step 120, a single condition for ambient temperature is confirmed from the four possibilities based on the measured temperature and low powers applied (LPs of e.g., 66%, 50%, 37% or 25% duty cycles) to the system from the algorithm by way of pre-determined pulse width adjustments. Greater duty cycle reflects greater amounts of energy calculated to maintain the system enthalpy, since energy is a product of power and time, whereas power is a product of voltage and current.

Upon determination of the ambient state at step 120, the method moves to step 122 where it is determined whether the measured ambient temperature is greater than 30° C. If the ambient temperature is not greater than 30° C., then the method moves to step 124A where the appropriate powers are re-calculated to reflect one of the AMB1 through AMB4 states by adjusting the duty-cycle of the heater pulses based on the ambient temperature measurement of step 118. At 124A, constant power is used, whereas the calculated energy for the four ambient states (AMB1 through AMB4) are proportional to the heater pulse-width, i.e., duty-cycle (ON versus OFF time). At higher ambient temperatures, it takes less energy to maintain steady state, since maintaining system enthalpy by providing warmth via one or more heat sources is desired. The exact percentages to calculate energy in the four ambient states (AMB1 through AMB4) can be determined experimentally. If the ambient temperature is determined to be less than 15° C. (AMB1), at step 124A low energy with duty-cycle of 66% is provided to the interactive enthalpy exchange system in order to maintain the enthalpy. If the ambient temperature is determined to be in a temperature range from 15° C. to 20° C. (AMB2), at step 124A low energy with duty-cycle of 50% is provided to the interactive enthalpy exchange system in order to maintain the enthalpy. If the ambient temperature is determined to be greater than 20° C. and up to 25° C. (AMB3), then the method continues to step 124A at which low energy with duty-cycle of 37% is provided to the interactive enthalpy exchange system in order to maintain the enthalpy. If the ambient temperature is determined to be greater than 25° C. and up to 30° C. (AMB4), then the method continues to step 124A at which low energy with duty-cycle of 25% is provided to the interactive enthalpy exchange system in order to maintain the enthalpy. If, however, at step 122 the ambient temperature is determined to be greater than 30° C., then the method continues to step 124B. At step 124B it is determined if the skin temperature of the infant is greater than or equal to 37.5° C. If the skin temperature of the infant is greater than or equal to 37.5° C., then the method moves to step 104 in which power is removed and an alarm is displayed at the display unit 52 of the control/display unit 44. If, however, the skin temperature of the infant is not greater than or equal to 37.5° C., then the method moves to step 102 and repeats.

In short, temperature deviations trigger software functions pre-programmed to check for infant, primary, secondary and ambient values, continually to ensure the system is functioning properly and within safe limits. Temperature feedback and resulting regulation to maintain infant body temperatures close to 37° C. is based on the skin temperature, continually monitored, for example, at the axilla (under the arm) or preferably the torso using a modified feedback-control theory based proportional-integration-derivative (PID) algorithm suited to this warming system. It is worth noting, modified PID algorithms may be used for different patient, the medium used in the primary heat source, secondary heat source and ambient temperature segment ranges; for example, ambient <15° C., 15-20° C., >20-25° C., >25-30° C. and >30° C., respectively. Regardless, when the infant skin temperature exceeds 37.5° C. or when the ambient surroundings exceed 30° C., power to the heater will immediately be cut to prevent overheating.

In addition, heater power and energy calculated by this modified PID algorithm can be up or down regulated, based on the low or high ambient environments (AMB1-AMB4 on FIG. 10), so as to maintain the primary temperature, and thus, the infant at steady-state. This additional regulation is important because elevated environments support overheating; whereas lower ambient environments support heat depletion, resulting in under-heating; either outcome negatively affects the patient. This can be dangerous when moving the infant from a colder environment, such as outside the house to the inside.

This ambient environment measurement feature was also useful in regulating power, i.e., maintaining adequate heater power without overheating. Pouches are often left open for extended periods of time when caregivers attend to the patient, or when a mother is feeding the infant. Software-independent hardware measures are incorporated to minimize risk while enhancing patient, operator and equipment safety. It is worth noting that several versions of the algorithm can be written by any skilled persons in the art. The operational flow-chart of FIG. 10 is a sample algorithm representation of the degrees of freedom available in determining constraints for temperature readings, obtained by the sensors (SN1 through SN4). Additional sensors can be added for redundancy to validate temperature measurements. Likewise, accurate power calculation and available battery charge are possible with voltage divider based resident circuits.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. An interactive enthalpy exchange system for infant care comprising:
   a pouch configured as a wrap, wherein the pouch is wrappable around an infant;
   a temperature sensor for measuring a skin temperature of the infant;
   a heat source arranged in the pouch, the heat source including a first heat source and a second heat source different from the first heat source; and
   control circuitry operatively coupled to the heat source, the control circuitry configured to control interactive enthalpy between the first heat source and the second heat source to maintain a temperature within the pouch at a prescribed temperature, the control circuitry further configured to control an amount of power provided to the heat source based on the skin temperature measured by the temperature sensor, wherein the control circuitry is configured to provide uniform heat transfer by conduction to the infant placed in the pouch by exchanging enthalpy among the heat sources based on a temperature outside the pouch.

2. A method for providing uniform thermal energy to an infant using an interactive enthalpy exchange system having a pouch configured as a wrap, wherein the pouch is wrappable around the infant, a heating device having a first heat source and a second heat source different from the first heat source, and control circuitry operatively coupled to the heating device, the method comprising:
   measuring a skin temperature of the infant;
   monitoring at least one of i) the measured skin temperature of the infant within the pouch, ii) a temperature external to the pouch, iii) a temperature of the first heat source, and iv) a temperature of the second heat source; and
   controlling enthalpy exchange between the first and second heat sources based on at least one of the measured skin temperature of the infant, the temperature of the first heat source, the temperature of the second heat source and the temperature external to the pouch to provide heat to the infant, said controlling including controlling an amount of power provided to the heating device based on the measured skin temperature;
   wherein controlling enthalpy exchange includes providing non-uniform thermal energy to the infant via enthalpy exchange between the first and second heat sources based on at least one of the skin temperature of the infant, the temperature of the first heat source, the temperature of the second heat source and the temperature external to the pouch, and wherein non-uniform thermal energy is provided selectively, depending on proximity of the pouch to an area of the infant;
   measuring an ambient temperature outside the pouch; and
   adjusting a duty cycle of power provided to the heating device based on the measured ambient temperature.

3. The method according to claim 2, further comprising heating the first heat source prior to use in the interactive enthalpy exchange system.

4. The method according to claim 2, further comprising generating an alarm when one of the skin temperature of the infant, the temperature of the first heat source, the temperature of the second heat source and the temperature external to the pouch, differs from a corresponding prescribed temperature by more than a prescribed value.

5. The method according to claim 4, wherein generating the alarm includes removing power from the second heat source.

6. An interactive enthalpy exchange system for infant care comprising:
   a pouch configured as a wrap, wherein the pouch is wrappable around an infant;
   a temperature sensor for measuring a skin temperature of the infant;
   a heat source arranged in the pouch, the heat source including a first heat source and a second heat source different from the first heat source; and
   control circuitry operatively coupled to the heat source, the control circuitry configured to control interactive enthalpy exchange between the first heat source and the second heat source to maintain a temperature within the pouch at a prescribed temperature, the control circuitry further configured to control an amount of power provided to the heat source based on the skin temperature measured by the temperature sensor; and
   an ambient temperature sensor for measuring an ambient temperature outside the pouch, wherein the control circuitry is further configured to adjust a duty cycle of power provided to the heat source based on the measured ambient temperature.

7. The system according to claim 1, further comprising a transporter electrically couplable to the second heat source and the control circuitry, the transporter including a battery for supplying power for the second heat source and the control circuitry.

8. The system according to claim 1, wherein the first and second heat sources are removable from the pouch.

9. The system according to claim 1, wherein the first heat source comprises a gel- based phase-change material.

10. The system according to claim 1, wherein the first heat source has a heat retention capacity of at least 200 J/g.

11. The system according to claim 1, wherein the second heat source comprises a resistive heating element.

12. The system according to claim 11, wherein the resistive heating element comprises a resistor and a switch electrically coupled to the resistor.

13. The system according to claim 12, wherein the resistor and the switch are connected to another resistor in parallel, wherein when the switch is closed current flow through the interactive enthalpy exchange system increases.

14. The system according to claim 11, wherein the resistive heating element comprises a plurality of resistors arranged in rungs, and two terminals connected to the rungs to provide a two-fold symmetrical connection operative to normalize current in each of the rungs.

15. The system according to claim 11, wherein the resistive heating element comprises a first set of resistors connected in series and a second set of resistors connected in series, the first set of resistors and the second set of resistors being connected in parallel with each other.

16. The system according to claim 1, wherein the second heat source comprises thermoelectric circuitry operable to cool the first heat source.

17. The system according to claim 1, wherein the control circuitry includes at least one sensor for obtaining one of a temperature outside the pouch, a temperature of the first heat source, or a temperature of the second heat source.

18. The system according to claim 1, wherein the pouch comprises material capable of withstanding a temperature variation ranging from −20° C. to 90° C.

19. The system according to claim 1, wherein the control circuitry includes a display device for displaying at least one of the skin temperature of the infant, a temperature outside the pouch, a temperature of the first heat source, or a temperature of the second heat source.

20. The system according to claim 1, wherein the control circuitry includes light emitting diodes for indicating system status and for providing a visual alarm when the system status is outside of a prescribed range.

21. The system according to claim 1, wherein the control circuitry includes an audio device for providing an audio alarm when system status is outside of a prescribed range.

22. The system according to claim 1, wherein the control circuitry controls the interactive enthalpy by transferring energy between the first and second heat sources.

\* \* \* \* \*